US006361818B2

(12) United States Patent
Biyani et al.

(10) Patent No.: US 6,361,818 B2
(45) Date of Patent: Mar. 26, 2002

(54) NUTRIENT RICH, LOW FAT, HIGH FIBER, CARROT PRODUCT, AND PROCESS OF MAKING

(76) Inventors: Milind Kesharlal Biyani, 11 Shivam Malabar Hill Road Mulund Colony, Mumbai (IN), 400082; Manisha Manohar Banavaliker, 7/4 Sahajeevan Soc.Barve Negar, Ghatkopar (West), Mumbai (IN), 400084; Geeta Chandravadan Parikh, Amrut Ashish, Jogeshwari (West), Mumbai (IN), 400060; Sushma Milind Biyani, 11 Shivam, Malabar Hill Road Mulund Colony, Mumbai (IN), 400082

( * ) Notice: Subject to any disclaimer, the term of this patent is extended or adjusted under 35 U.S.C. 154(b) by 0 days.

(21) Appl. No.: 09/729,356

(22) Filed: Dec. 5, 2000

Related U.S. Application Data

(63) Continuation of application No. PCT/IN00/00007, filed on Jan. 28, 2000.

(30) Foreign Application Priority Data

Jan. 29, 1999 (IN) .......................................... 71/BOM/99

(51) Int. Cl.$^7$ ............................................... A23L 1/212
(52) U.S. Cl. ........................ 426/640; 426/489; 426/492; 426/518; 426/639
(58) Field of Search ................................. 426/639, 640, 426/489, 492, 518

(56) References Cited

U.S. PATENT DOCUMENTS

| | | | | |
|---|---|---|---|---|
| 2,596,662 A | * | 5/1952 | Ducker et al. ............... | 426/639 |
| 2,739,145 A | | 3/1956 | Barnett ........................ | 260/112 |
| 3,894,157 A | | 7/1975 | Gottlieb et al. ............. | 426/268 |
| 4,372,984 A | | 2/1983 | Bauer ........................ | 426/637 |
| 4,447,460 A | * | 5/1984 | Lewis et al. ................. | 426/639 |
| 4,770,880 A | | 9/1988 | Sasaki et al. ............ | 424/195.1 |
| 4,789,553 A | | 12/1988 | McIntyre et al. ........... | 426/325 |
| 4,956,187 A | | 9/1990 | Ishigaki ....................... | 426/46 |
| 5,304,374 A | | 4/1994 | Graves et al. ........... | 424/195.1 |
| 5,354,851 A | | 10/1994 | Graves .......................... | 536/2 |
| 5,403,612 A | | 4/1995 | Huang ........................ | 426/577 |
| 6,231,866 B1 | * | 5/2001 | Mann .......................... | 426/639 |

FOREIGN PATENT DOCUMENTS

| | | |
|---|---|---|
| EP | 0 478 401 A2 | 4/1992 |
| IN | 183668 | 11/1996 |
| JP | 1281056 | 11/1989 |
| JP | 09023859 | 1/1997 |

OTHER PUBLICATIONS (XP–002144556) B. Bao and K.C. Chang "Carrol Pulp Chemical Composition, Color, and Water–holding Capacity as Affected by Blanching", Journal of Food Science vol. 59, No. 6 pp. 1159–1161 (1994).

(XP–000923083) Karl Herrmann "Inhaltsstoffe de Möhren", Industrielle Obst, vol. 80, No. 7 pp. 266–274.

Carrot Pulp Chemical Composition, Color, and Water–Holding Capacity as Affected by Blanching, Bao et al., J. Food Science, vol. 59, No. 6, 1994, pp. 1159–1161.

Fibre–Mediated Physiological Effects of Raw and Processed Carrots in Humans, Wisker et al., Br. J. Nutr., vol. 72, Oct. 1994, pp. 579–599 (abstract only).

Diet as a Risk Factor for Peripheral Arterial Disease in the General Population: The Edinburgh Artery Study, Donnan et al., Am. J. Clin. Nutr., vol. 57, 1993, pp. 917–921.

Binding of Dietary Anions to Vegatable Fiber, Hoagland, J. Agric. Food Chem., vol. 35, 1989, pp. 316–319.

Influence of Experimental Diets on Cholesterol and Triglyceride Levels of Rabbit Blood Serum Lipoproteins, Wehr et al., Act. Physiol. Pol., vol. 39, May–Jun. 1988, pp. 202–209 (abstract only).

Cobinding of Bile Acids to Carrot Fiber, Hoagland et al., J. Agric. Food Chem., vol. 37, 1989, pp. 316–319.

Dietary Fiber Constituants of Selected Fruits and Vegatables, Ross et al., J. Am. Diet. Assoc., vol. 85, Sep. 1985, pp. 1111–1116 (abstract only).

Effects of Processing on the Dietary Fiber Content of Wheat Bran, Pureed Green Beans, and Carrots, Anderson et al., Journal of Food Science, vol. 45, 1980, pp. 1533–1534.

The Effect of Raw Carrot on Scrum Lipids and Colon Function, Robertson et al., Am. J. Clin. Nutr., vol. 32, 19979, pp. 1989–1992 (abstract only).

Colonic Response to Dietary Fibre from Carrot, Cabbage, Apple, Bran and Guar Gum, Cummings et al., The Lancet, vol. 1, Jan. 7, 1978, pp. 5–9.

\* cited by examiner

*Primary Examiner*—Helen Pratt
(74) *Attorney, Agent, or Firm*—Pennie & Edmonds LLP

(57) ABSTRACT

Nutrient rich, low fat, high fiber, carrot product containing 20–50% by weight of fiber of which 15–40% by weight is insoluble and 5–10% by weight is soluble, 0.1–1.0% by weight of fat, 10–55% by weight of carbohydrates, 0.02–1% by weight of carotenoids and vitamins and 5–10% by weight of minerals and trace elements. A process for the preparation of the carrot product requires the step of stabilizing carrot juice with carbohydrate in amounts ranging from 1–10% by weight of the juice. A formulation of the carrot product mixed with excipients.

22 Claims, No Drawings

NUTRIENT RICH, LOW FAT, HIGH FIBER, CARROT PRODUCT, AND PROCESS OF MAKING

RELATED APPLICATIONS

This is a continuation of PCT application no PCT/IN00/00007, filed on Jan. 28, 2000.

FIELD OF THE INVENTION

This invention relates to nutrients rich low fat high fiber carrot product. It also relates to a process for the preparation of the carrot product and a formulation comprising the same.

BACKGROUND OF THE INVENTION

The therapeutic and nutritious effects of diets rich in fruits, and vegetables in general and carrots (*Daucus carota*) in particular are well known. "Effects of processing on the dietary fiber content of wheat bran, pureed green beans and carrots". Journal of food Science, 1980, 45, 1533–1534. N. E. Anderson and F. M. Clydesdale. "Fiber-mediated physiological effects of raw and processed carrots in humans", Br. J Nutr., 1994 72:579–599; Wisker E., Schweiizer T. F. et al. "Influence of experimental diets on cholesterol and triglyceride levels of rabbit blood serum lipoproteins", Acta. Physiol. Pol. 1988 39:202–206; Wehr H., Naruszewicz M. et al. "Dietary Fiber constitutes of selected fruits and vegetables". J. Am. Diet. Assoc., 1985:85: 1111–1116; Ross. J. K. et al. "The effect of raw carrot on serum lipids and colon function" Am. J. Clin Nutr., 1979; 32:1889–92; Robertson J., Brydon W. G. et al. "Colonic response to dietary fiber from carrot, cabbage, apple, bran." Lancet 1978; 1 (8054) :5–9; Cummings J. H., Branch W. et al. "Carrot pulp chemical composition, colour, and water holding capacity as affected by blanching". J Food Science, 1994; 59; 1159–1164; B. Bao and K. C. Chang. "Binding of dietary anions to vegetable fiber." J. Agric. Food Chem. 1989, 37, 1343–1347; Peter D. Hoagland. "Cobinding of bile acids to carrot fiber" J. Agric. Food Chem. 1987 35, 316–319; Peter D. Hoagland, Philip E. Pfeffer, "Diet as a risk factor for peripheral arterial disease in the general population: The Edinbourgh Artery Study", Am J Clin Nutr, 1993 57; 917–921, Peter T Donnan et al.

Diets rich in fiber and low in fat are in modern times recommended to be medically useful for subnormal mammalian conditions of different etiologies. For instance, they counter the harmful effects of fiber-deficient diets responsible for constipation, diverticulosis or irritable bowel syndrome (IBS). Diets low in fat and rich in fiber reduce cholesterol and triglyceride levels, coronary heart disease mortality and overall risk of cancer. A high fiber diet is important in pregnancy, old age and during the convalescence period following a heart attack. High fiber diets help in obesity treatment by decreasing meal-size and giving a sense of fullness and early satiation. Natural products such as vegetables and fruits are invariable sources of fiber. Especially well known high fiber products are those prepared from isapgol (*Plantago ovata*) or bran from, for example, oat or wheat.

Holistic systems of medicine such as the Ayurvedic system of medicine have for centuries been advocating the synergistic value of dispensing not just pure natural product ingredients but the complete set of nutrients as they are present in the natural source, a concept rapidly gaining new supporters in modern medicine.

Carrots are a unique natural source for providing a dietary fiber product for several reasons. Carrot fiber comprises both soluble fiber and insoluble fiber. This quality is unlike that found in fiber from isapgol and guar-gum (cyamopsis tetragonoloba) which contain mostly soluble fiber and fiber found in bran is mostly insoluble fiber. Soluble fiber is valuable for the management of hypercholesteremia. Insoluble fiber is most likely to benefit patients with atonic motor disorder. Insoluble fiber slows intestinal propulsion and is useful for diarrhoea affected IBS patients, whereas the action of the soluble part of the fiber is variable. The protective effect of insoluble fiber in lessening the risk of colon cancer is attributed to its dilution of colon contents. Carrot fiber contains lignin only in traces and is high in pectin content. The soluble fiber consists principally of a special type of pectin which reduces glucose uptake. The pectin fraction is composed not only of molecules with randomly distributed carboxyl groups but also of at least 50% of pectin molecules in which blocks of free carboxylic groups are available. Carrot fibers are especially effective in binding bile acids and reducing cholesterol levels. Carrot fiber constituents are highly fermentable producing short chain fatty acids known to decrease the rate of synthesis of cholesterol and glucose and to inhibit cancer. Therapeutic effects of carrots on human eyes are also known. Fresh carrots are, however, required to be consumed in very large quantities for therapeutic benefits. There is no standard or set limit of quantity to be consumed for such benefits.

U.S. Pat. No. 5,403,612 is concerned with a phosphorylated pectin-containing fiber product which is a low-cost, crude, human-consumable, pectin-containing fiber possessing the gelling effects of fully refined pectin. Fiber obtained from a food such as applies, barley, carrots, corn, grapefruit, oats, oranges, peas, rice, sugarbeet, sugar cane and wheat is treated with a dissociable phosphate reactant followed by removal of excess water from the treated fiber and drying thereof.

U.S. Pat. No. 5,354,851 relates to a low-cost, crude, human-consumable, pectic material containing fiber. Fiber obtained from fruits such as apples, lemons, oranges, and grapes, vegetables such as carrots and sugar beets and grasses such as sugar cane is treated with a reactant capable of chemically coupling alkaline earth metal ions to the exposed pectin on fiber.

U.S. Pat. No. 5,304,374 describes an edible pulp having enhanced hypocholesterolemic effect. The natural bile acid binding capacity of edible pulp material from fruits such as apples, oranges and grapes, vegetables such as carrots, corn, peas and sugar beets, grains such as barley, oats, rice and wheat and grasses such as sugar cane is enhanced by heating an aqueous slurry of the pulp material to at least 40° C. and/or sequentially reacting the pulp material with a reactant such as sodium hydroxide for activating the pendant groups on the polysaccharide component followed by addition of calcium chloride at a pH of less than about 7.

U.S. Pat. No. 4,956,187 describes iron enriched food products. Pulverised soyabean or carrot or a mixture of the two is hydrolysed with saccharide-decomposing enzyme and an iron compound is added to the hydrolysate followed by inoculation with yeast. The food products contain iron in readily absorbable and adverse reaction-free form and are useful as meal for patients.

U.S. Pat. No. 4,789,553 is concerned with chemical sterilisation and prevention of discolouration of low acid heat-sensitive foodstuffs such as low acid heat-sensitive vegetables and cereal grain products such as carrots, zucchini, asparagus, spears, cauliflower, yellow squash, rice, potatoes or cantaloupes by treatment with gluconic acid and its lactones whereby flavour, colour or texture of the foodstuffs is retained.

U.S. Pat. No. 4,770,880 relates to a fiber-rich vegetable material capable of absorbing mutagen. Fibers from vegetables are separated, boiled, washed with water and dewatered followed by dehydration involving co-drying the fibers with carrier materials. It gives an ingestible product including fiber-rich vegetable material made from cabbage, radish, bamboo sprout, onion, carrot, pimiento, spinach, soyabean malt, and asparagus.

U.S. Pat. No. 4,372,984 is concerned with improvement of consistency of reconstituted instant puree of vegetables. Crude vegetable fibers such as fibers of tubers, cereals or fruits are incorporated in an instant puree, for example a potato, carrot or split pea puree in quantities of at most 10% by dry weight of fibers based on the dry matter content of the puree. Crude fibers are suspended in water, sterilised by steam injection, cooled and dryed.

U.S. Pat. No. 3,894,157 describes colour stabilisation in freeze-dried carrots with ascorbic and erythorbic acids. An aqueous ascorbic or erythorbic acid solution infused throughout decorticated, blanched subdivided carrots just prior to freezing effects reduction of colour loss in freeze-dried carrot during storage.

U.S. Pat. No. 2,739,145 is concerned with recovery of carotene, fiber and serum from carrots. Fresh carotene containing material is mechanically pulped with serum from previous lot and coagulated particles are separated out. Fiber is separated from serum by steam. Excess serum may be concentrated by evaporation or used without concentration in various culturing operations as a biotic medium. On evaporation of the carrots serum by pan methods a carrot syrup is obtained.

One of the inventors namely Dr Biyani had earlier developed a process for manufacture of low fat high fiber carrot granules, in which fat-content of disintegrated carrots is reduced by removing lipoid particles with the help of carboxylic acids and the remaining material is dried below 60° C. to get the fibrous product in granular form [Indian Patent Application No 183668]. It has been found that during drying, carotenoids in the product degrade as a result of which carotenoids content in the dehydrated product is very low and it is unstable during storage.

To the best of our knowledge and information to date there is no report of any standardised carrot product containing therapeutically and nutritiously effective and useful optimal amounts of nutrients and fiber content.

OBJECTS AND SUMMARY OF THE INVENTION

An object of the invention is to provide a nutrients rich low fat high fiber carrot product.

Another object of the invention is to provide a nutrients rich low fat high fiber carrot product which is particularly rich in carotenoids and retains natural colour of carrot.

Another object of the invention is to provide a process for the preparation of a nutrients rich low fat high fiber carrot product.

Another object of the invention is to provide a process for the preparation of a nutrients rich low fat high fiber carrot product which is particularly rich in carotenoids and retains natural colour of carotenoids.

Another object of the invention is to provide a formulation of a nutrients rich low fat high fiber carrot product.

Another object of the invention is to provide a formulation of a nutrients rich low fat high fiber carrot product which is particularly rich in carotenoids and retains natural colour of carrot.

Another object of the invention is to provide a formulation of a nutrients rich low fat high fiber carrot product in the form of chewable granules, tablet, powder or diskettes/wafers.

DETAILED DESCRIPTION OF THE INVENTION

According to the invention there is provided nutrients rich low fat, high fiber carrot product comprising 20–50% by weight of fiber of which 15–40% by weight is insoluble and 5–10% by weight is soluble, 0.1–1.0% by weight of fat, 10–55% by weight of carbohydrates, 0.02–1% by weight of carotenoids and vitamins and 5–10% by weight of minerals and trace elements.

Preferably the nutrients rich low fat high fiber carrot product comprises 25 to 45% by weight of fiber of which 20 to 35% by weight is insoluble and 5 to 10% by weight is soluble, 0.3 to 0.7% by weight of fat, 20 to 40% by weight of carbohydrates, 0.1 to 0.5% by weight of carotenoids and vitamins and 6 to 8% by weight of minerals and trace elements.

The vitamins include vitamin B1, vitamin B2, vitamin C and/or niacin and carotenoids include beta-carotene and/or alpha-carotene and minerals and trace elements include iron, zinc, magnesium, potassium, sodium, phosphorus, manganese and/or calcium.

According to the invention there is also provided a process for the preparation of nutrients rich low fat high fiber carrot product comprising 20–50% by weight fiber of which 15–40% by weight is insoluble and 5–10% by weight is soluble, 0.1–1.0% by weight of fat, 10–55% by weight of carbohydrates, 0.02–1% by weight of carotenoids and vitamins and 5–10% by weight of minerals and trace elements, the process comprising crushing carrots, pressing the crush to separate pomace from juice, adjusting the pH of the juice to 3.0 to 6.0 with carboxylic acid in an amount of acid equivalent to 0.03 to 3% by weight of the juice, stabilising the juice with carbohydrate in amounts ranging from 1–10% by weight of the juice, separating the supernatent from the residual matter, concentrating the supernatent, blending the concentrate with the previously isolated pomace, drying the blend, pulverising or granulating the blend and sieving the powder or granules.

According to an embodiment of the invention the process comprises preparation of a carrot product comprising 25 to 45% by weight of fiber of which 20 to 35% by weight is insoluble and 5 to 10% by weight is soluble, 0.3 to 0.7% by weight of fat, 20 to 40% by weight of carbohydrates, 0.1 to 0.5% by weight of carotenoids and vitamins and 6 to 8% by weight of minerals and trace elements.

The carboxylic acid is in solid form or in the form of a saturated aqueous solution preferably in an amount of acid equivalent to 0.02 to 1% by weight of the juice. The carboxylic acid is monocarboxylic acid such as ascorbic acid or dicarboxylic acid such as adipic acid, malic acid, fumaric acid or tartaric acid or tricarboxylic acid such as citric acid or mixture thereof. Preferably a mixture of ascorbic acid with adipic acid or malic acid or fumaric acid or tartaric acid and/or citric acid is used to adjust the pH of the juice. Preferably the pH of the juice is adjusted to 5.0.

The carbohydrate is in solid form or in the form of a saturated aqueous solution in an amount preferably ranging from 5.0 to 8.0% by weight of the juice. The carbohydrate is monosaccharide selected from fructose or dextrose or polysaccharide selected from sucrose or lactose or hexitol selected from mannitol or sorbitol. Preferably a mixture of fructose and dextrose or sucrose and lactose and/or mannitol and sorbitol is added to the juice.

The supernatent is separated from the residual matter by centrifugation of filtration.

The supernatent is concentrated by vacuum distillation at 50 to 60° C.

The blend is dried at 50 to 60° C. in a dryer such as tray dryer or rotary dryer under high vacuum. The blend is pulverised in a pulveriser such as multimill or granulated in a granulator such as vertical or horizontal granulator. The powder or granules may be sieved through sieves of mesh sizes ranging from 10 to 100, preferably 20 to 80.

According to the invention there is also provided a formulation of a nutrients rich low fat, high fiber carrot product comprising 20–50% by weight fiber of which 15–40% by weight is insoluble and 5–10% by weight is soluble, 0.1–1.0% by weight of fat, 10–55% by weight of carbohydrates, 0.02–1% by weight of carotenoids and vitamins and 5–10% by weight of minerals and trace elements mixed with excipients.

Preferably the formulation of a nutrients rich low fat high fiber carrot product comprises 25 to 45% by weight of fiber of which 20 to 35% by weight is insoluble, and 5 to 10% by weight is soluble, 0.3 to 0.7% by weight of fat, 20 to 40% by weight of carbohydrates, 0.1 to 0.5% by weight of carotenoids and vitamins and 6 to 8% by weight of minerals and trace elements.

The formulation may be in the form of chewable granules, powder or diskettes/wafers.

The excipients are, for example, sucrose, citric acid, orange oil, gum acacia, aspartame or sodium saccharin.

According to the invention the carrot product or formulation of carrot product is standardised such that it contains therapeutically and nutritiously effective and useful optimal amounts of nutrients and fiber. Due to stabilisation with carbohydrates, the product is enriched with carotenoids and its colour is retained. It may be dispensed and consumed conveniently in small doses in healthcare and nutrition applications in the prevention and treatment of constipation, irritable bowel syndrome, obesity, diabetes, high cholesterol, cardiovascular diseases, cancer or eye diseases. It thus obviates the necessity of having to consume large quantities of fresh carrots for therapeutic and nutritional effects.

The following experimental examples illustrate the invention but do not limit the scope thereof:

EXAMPLE 1

Fresh, hard, good quality reddish orange coloured carrots (*Daucus carota*) with a smooth surface were selected and washed thoroughly with water. The washed carrots (1.0 kg) were subjected to crushing in a crusher to provide a crush which was subjected to pressing through a filter press to provide pomace (380 grams) and liquid juice (ca. 600 ml). To the liquid juice, 1 g of adipic acid was added with stirring to adjust the pH to 4.0 followed by 10 g of sorbitol and it was subjected to centrifugation to provide a clear liquid extract (580 ml). The liquid extract was concentrated by vacuum distillation at 50–60° C. to get a concentrate (about 100 ml) which was blended with the previously isolated pomace and dried at 50–60° C. in a tray dryer under vacuum. The dried material was passed through a granulator and sieved through 20 mesh to obtain nutrients rich low fat high fiber carrot granules (95 g). The composition of the granules per 100 g was as given below:

| Insoluble Fiber | 25 g |
| Soluble Fiber | 7 g |
| Total Fiber | 32 g |
| Carbohydrates | 25 g |
| Fat | 0.67 g |
| Proteins | 7.5 g |
| Carotenoids | 87 mg |
| Vitamin B1 | 1 mg |
| Vitamin B2 | 0.02 mg |
| Vitamin C | 8 mg |
| Calcium | 1.46 g |
| Magnesium | 580 mg |
| Iron | 2 mg |
| Manganese | 1 mg |
| Zinc | 1 mg |
| Potassium | 2.99 g |
| Sodium | 1.79 g |
| Phosphorus | 277 mg |
| Total Minerals (Ash value) | 8.8 g |

The granules had natural reddish orange colour of the carrots.

EXAMPLE 1A

In an experiment similar to Example 1 without the addition of sorbitol, the carrot granules obtained were light in colour and had a carotenoids content of 6 mg per 100 g.

EXAMPLE 2

Fresh, hard, good quality orange coloured carrots (*Daucus carota*) with a smooth surface were selected and washed thoroughly with water. The washed carrots (1.0 kg) were processed according to the procedure described in Example 1 to obtain 95 g granules. The composition of the granules per 100 g was as given below:

| Insoluble Fiber | 20 g |
| Soluble Fiber | 13 g |
| Total Fiber | 33 g |
| Carbohydrates | 21 g |
| Fat | 0.7 g |
| Proteins | 6.9 g |
| Carotenoids | 92 mg |
| Vitamin B1 | 0.7 mg |
| Vitamin B2 | 0.03 mg |
| Vitamin C | 11 mg |
| Calcium | 0.6 g |
| Magnesium | 122 mg |
| Iron | 14 mg |
| Manganese | 0.5 mg |
| Zinc | 0.8 mg |
| Potassium | 1.1 g |
| Sodium | 1.59 g |
| Phosphorus | 416 mg |
| Total Minerals (Ash value) | 7.4 g |

The granules had natural orange colour of the carrots.

EXAMPLE 2A

In an experiment similar to Example 2 without the addition of sorbitol, the carrot granules obtained were light in colour and had a carotenoids content of 7 mg per 100 g.

EXAMPLE 3

The procedure described in Example 1 was followed using citric acid in the place of adipic acid.

EXAMPLE 4

The procedure described in Example 1 was followed using fumaric acid in the place of adipic acid.

EXAMPLE 5

The procedure described in Example 1 was followed using malic acid in the place of adipic acid.

EXAMPLE 6

The procedure described in Example 1 was followed using tartaric acid in the place of adipic acid.

EXAMPLE 7

The procedure described in Example 1 was followed using ascorbic acid in the place of adipic acid.

EXAMPLE 8

The procedure described in Example 1 was followed using mannitol in the place of sorbitol.

EXAMPLE 9

The procedure described in Example 1 was followed using sucrose in the place of sorbitol.

EXAMPLE 10

The procedure described in Example 1 was followed using lactose in the place of sorbitol.

EXAMPLE 11

The procedure described in Example 1 was followed using dextrose in the place of sorbitol.

The composition of the granules of Examples 3 to 11 was found to lie in the range given below per 100 gm of the product:

| | |
|---|---|
| Insoluble Fiber | 15–40 g |
| Soluble Fiber | 5–10 g |
| Total Fiber | 20–50 g |
| Carbohydrates | 10–55 g |
| Fat | 0.1–1 g |
| Proteins | 4–9 mg |
| Carotenoids | 20–100 mg |
| Vitamin B1 | 0.1–2 mg |
| Vitamin B2 | 0.01–1 mg |
| Vitamin C | 2–1000 mg |
| Calcium | 0.3–2 g |
| Magnesium | 0.1–1 mg |
| Iron | 1–25 mg |
| Manganese | 0.1–1 g |
| Zinc | 0.1–2 mg |
| Potassium | 1–4 g |
| Sodium | 1–3 g |
| Phosphorus | 100–500 mg |
| Total Minerals (Ash value) | 5–10 g |

The granules of Examples 3 to 11 had natural reddish orange colour of the carrots.

EXAMPLE 11A

In Experiments similar to Examples 3 to 11 without the addition of dextrose, lactose, mannitol, sorbitol or sucrose, the carrot granules were light in colour and had a carotenoids content of 1 to 8 mg per 100 g.

EXAMPLE 12

Sucrose (29.7 g) and citric acid (0.2 g) were dissolved in equal amount of water and sprayed on the carrot granules of Example 1 (70 g). The granules were dried at 50 to 60° C. in a tray drier under vacuum and cooled to ambient temperature. Orange oil (0.09 g) and gum acacia (0.01 g) were suspended in 1 ml of water and sprayed on the granules and blended for five minutes to obtain chewable granules.

EXAMPLE 13

The procedure in Example 12 was followed using 0.2 g aspartame in the place of sucrose.

EXAMPLE 14

The procedure in Example 12 was followed using 0.1 g sodium saccharin in the place of sucrose.

EXAMPLE 15

The granules of Example 1 (60 g) were powdered to 30 mesh and mixed with sucrose powder (38.8 g). The mixture was granulated with gum acacia (0.9 g) and citric acid (0.2 g) in water (10 ml) and dried at 50 to 60° C. in a tray drier under vacuum. Dried granules were flavoured by mixing with orange oil (0.1 g) and compressed into diskettes/wafers.

EXAMPLE 16

The granules of Example 1 (99 g) were pulverised to 100 mesh powder. Aspartame (0.6 g), citric acid (0.3 g), orange oil (0.09 g) and gum acacia (0.01 g) were mixed with 10 times water and sprayed on the powder, mixed and blended for five minutes. The powder is made into suspension in water (100 to 200 ml) for use.

EXAMPLE 17

One dose of 10 gm of the granules of Example 1 followed by a glass of water was daily given to a first group of 12 persons after meal for a period of 1 month. Similarly one dose of 10 gms of granules of Example 1A was daily given to a second group of 12 persons after meal for a period of 1 month. After 1 month 8 persons out of 12 in the first group reported reduction in sensitivity of eyes to bright sunlight, whereas none in the second group reported any such benefit.

EXAMPLE 18

One dose of 10 g of the granules of Example 1 followed by a glass of water was daily given to a first group of 18 obese persons (Group I) 15 minutes before each meal for a period of 2 months. Similarly one dose of 10 g of Isapgol powder followed by a glass of water was daily given to a second group of 18 obese persons (Group II) 15 minutes before each meal for a period of 2 months. The food served at each meal was the same and its consumption by each group was noted. It was observed that the amount of food consumed by the Group I gradually reduced. It was inferred that leisurely chewing of the granules gave a feeling of satiety and the water gave a feeling of fullness due to swelling of the fibre. As a result, the Group I was not able to consume the same quantity of food throughout the period of the experiment. Weight reduction of 2–3 Kg was observed in 15 persons of the Group I. Decreased consumption of food and reduction in weight did not result in weakness or fatigue of the concerned persons. It was inferred that this is due to the presence of nutrients in the granules. In the case of Group II, there was no significant reduction in consumption of food or in weight.

What is claimed is:

1. A low fat, high fiber carrot product which is rich in nutrients comprising 20–50% by weight of fiber of which 15–40% by weight is insoluble and 5–10% by weight is soluble, 0.1–1.0% by weight of fat, 10–55% by weight of carbohydrates, 0.02–1% by weight of carotenoids and vitamins and 5–10% by weight of minerals and trace elements.

2. The low fat, high fiber carrot product which is rich in nutrients of claim 1 which comprises 25 to 45% by weight of fiber of which 20 to 35% by weight is insoluble and 5 to 10% by weight is soluble, 0.3 to 0.7% by weight of fat, 20 to 40% by weight of carbohydrates, 0.1 to 0.5% by weight of carotenoids and vitamins and 6 to 8% by weight of minerals and trace elements.

3. The low fat, high fiber carrot product which is rich in nutrients of claim 1, in which the vitamins are vitamin B2, vitamin C and/or niacin and carotenoids are beta-carotene and/or alpha-carotene and minerals and trace elements are iron, zinc, magnesium, potassium, sodium, phosphorus, manganese and/or calcium.

4. A process for preparing a low fat, high fiber carrot product which is rich in nutrients comprising 20–50% by weight fiber of which 15–40% by weight is insoluble and 5–10% by weight is soluble, 0.1–1.0% by weight of fat, 10–55% by weight of carbohydrates, 0.02–1% by weight of carotenoids and vitamins and 5–10% by weight of minerals and trace elements, the process comprising crushing carrots, pressing the crushed carrots to separate pomace from juice, adjusting the pH of the juice to a value of 3.0 to 6.0 with a carboxylic acid wherein the amount of acid is equivalent to 0.03 to 3% by weight of the juice, stabilizing the juice with a carbohydrate in an amount ranging from 1–10% by weight of the juice, separating residual matter from the juice to provide a clarified supernatant, concentrating the clarified supernatant to provide a concentrate, blending the concentrate with the previously isolated pomace to provide a blend, drying the blend, pulverizing or granulating the blend to provide granules, and sieving the granules.

5. A process as claimed in claim 4, which comprises preparation of a carrot product comprising 25 to 45% by weight of fiber of which 20 to 35% by weight is insoluble and 5 to 10% by weight is soluble, 0.3 to 0.7% by weight of fat, 20 to 40% by weight of carbohydrates, 0.1 to 0.5% by weight of carotenoids and vitamins and 6 to 8% by weight of minerals and trace elements.

6. A process as claimed in claim r, wherein the carboxylic acid is in solid form or in the form of a saturated aqueous solution in an amount of acid equivalent to 0.2 to 1% by weight of the juice.

7. A process as claimed in claim 4, wherein the pH of the juice is adjusted to 5.0.

8. A process as claimed in claim 4, wherein the carboxylic acid is a monocarboxylic acid, a dicarboxylic acid, or a tricarboxylic acid.

9. A process as claimed in claim 8, wherein the carboxylic acid is one or more of ascorbic acid, adipic acid, malic acid, fumaric acid, tartaric acid or citric acid.

10. A process as claimed in claim 4, wherein the carboxylic acid is a mixture of ascorbic acid with adipic acid or malic acid or fumaric acid or tartaric acid and/or citric acid.

11. A process as claimed in claim 4, wherein the carbohydrate is in solid form or in the form of a saturated aqueous solution in an amount ranging from 5.0 to 8.0% by weight of the juice.

12. A process as claimed in claim 4, wherein the carbohydrate is a monosaccharide, polysaccharide, or hexitol.

13. A process as claimed in claim 12, wherein the carbohydrate is one or more of fructose, dextrose, sucrose, lactose, mannitol or sorbitol.

14. A process as claimed in claim 4, wherein the carbohydrate is a mixture of fructose and dextrose or sucrose and lactose and/or mannitol and sorbitol.

15. A process as claimed in claim 4, wherein the supernatent is separated from the residual matter by centrifugation or filtration.

16. A process as claimed in claim 4, wherein the supernatent is concentrated by vacuum distillation at 50 to 60° C.

17. A process as claimed in claim 4, wherein the blend is dried at 50 to 60° C. under high vacuum.

18. A low fat, high fiber carrot product which is rich in nutrients comprising 20–50% by weight fiber of which 15–40% by weight is insoluble and 5–10% by weight is soluble, 0.1–1.0% by weight of fat, 10–55% by weight of carbohydrates, 0.02–1% by weight of carotenoids and vitamins and 5–10% by weight of minerals and trace elements mixed with excipients.

19. The low fat, high fiber carrot product which is rich is in nutrients of claim 18 comprising 25 to 45% by weight of fiber of which 20 to 35% by weight is insoluble and 5 to 10% by weight is soluble, 0.3 to 0.7% by weight of fat, 20 to 40% by weight of carbohydrates, 0.1 to 0.5% by weight of carotenoids and vitamins and 6 to 8% by weight of minerals and trace elements.

20. The low fat, high fiber carrot product which is rich in nutrients of claim 18 which is in the form of chewable granules, powder or diskettes/wafers.

21. A process for preparing a low fat, high fiber carrot product which is rich in nutrients comprising:

crushing carrots to provide crushed carrots;

pressing the crushed carrots to separate pomace from juice;

adjusting the pH of the juice to a value of 3.0 to 6.0 with a carboxylic acid;

stabilising the juice with a carbohydrate;

separating residual matter from the juice to provide a clarified supernatant;

concentrating the clarified supernatant to provide a concentrate;

blending the concentrate with the previously isolated pomace to provide a blend;

drying the blend; and pulverizing or granulating the blend to provide granules.

22. A process for preparing a low fat, high fiber carrot product which is rich in nutrients comprising:

crushing carrots to provide crushed carrots;

pressing the crushed carrots to separate pomace from juice;

adjusting the pH of the juice to a value of 3.0 to 6.0 with a carboxylic acid;

separating residual matter from the juice to provide a clarified supernatant;

concentrating the clarified supernatant to provide a concentrate;

blending the concentrate with the previously isolated pomace to provide a blend;

drying the blend; and pulverizing or granulating the blend to provide granules; the improvement comprising stabilizing the juice with a carbohydrate in an amount ranging from 1–10% by weight of the juice after the juice is acidified to provide a low fat, high fiber carrot product which is rich in nutrients having an elevated amount of carotenoids.

* * * * *